United States Patent
Bloem

(10) Patent No.: US 8,587,426 B2
(45) Date of Patent: Nov. 19, 2013

(54) IMPLANTABLE MEDICAL DEVICE WITH ADAPTIVE SIGNAL PROCESSING AND ARTIFACT CANCELLATION

(75) Inventor: David R. Bloem, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 972 days.

(21) Appl. No.: 12/687,936

(22) Filed: Jan. 15, 2010

(65) Prior Publication Data

US 2010/0179395 A1 Jul. 15, 2010

Related U.S. Application Data

(60) Provisional application No. 61/144,943, filed on Jan. 15, 2009.

(51) Int. Cl.
*G08B 1/08* (2006.01)

(52) U.S. Cl.
USPC .............. 340/539.12; 340/539.11; 340/573.1; 600/301

(58) Field of Classification Search
USPC ..................... 340/539.12; 600/301
See application file for complete search history.

(56) References Cited

U.S. PATENT DOCUMENTS

| | | | |
|---|---|---|---|
| 5,423,869 A | 6/1995 | Poore et al. | |
| 6,115,628 A | 9/2000 | Stadler et al. | |
| 6,198,952 B1 | 3/2001 | Miesel | |
| 6,408,198 B1 | 6/2002 | Hanna et al. | |
| 6,497,655 B1 | 12/2002 | Linberg et al. | |
| 7,814,324 B2 * | 10/2010 | Blakley et al. | ................ 713/176 |
| 2003/0065269 A1 | 4/2003 | Vetter et al. | |
| 2004/0230105 A1 | 11/2004 | Geva et al. | |
| 2004/0230128 A1 * | 11/2004 | Brockway et al. | ............ 600/510 |
| 2005/0049492 A1 | 3/2005 | Sweeney et al. | |
| 2005/0197586 A1 | 9/2005 | Pearlman | |
| 2006/0064136 A1 | 3/2006 | Wang | |
| 2006/0116593 A1 | 6/2006 | Zhang et al. | |
| 2006/0211949 A1 | 9/2006 | Sweeney et al. | |
| 2007/0208265 A1 | 9/2007 | Coudere et al. | |
| 2008/0051670 A1 | 2/2008 | Banet et al. | |
| 2008/0132799 A1 | 6/2008 | Xue | |
| 2008/0221401 A1 | 9/2008 | Derchak et al. | |

FOREIGN PATENT DOCUMENTS

| | | |
|---|---|---|
| WO | 2004091719 | 10/2004 |
| WO | 2008064682 | 6/2008 |

OTHER PUBLICATIONS

Manly, Bryan F.J., Multivariate Statistical Methods: A Primer 3rd Edition, Chapman & Hall, 2004, pp. 75-90.
(PCT/US2010/021126) PCT Notification of Transmittal of the International Search Report and the Written Opinion of the International Search Authority, Mailed Mar. 29, 2010, 10 pages.
(PCT/US2010/021124) PCT Notification of Transmittal of the International Search Report and the Written Opinion of the International Search Authority, Mailed Mar. 29, 2010, 10 pages.

* cited by examiner

*Primary Examiner* — Kerri McNally
(74) *Attorney, Agent, or Firm* — Evans M. Mburu; Stephen W. Bauer

(57) ABSTRACT

A medical device includes multiple sensors used to acquire sensor signals grouped into multiple sets to obtain multiple multi-dimensional signals. Principal component analysis of the multi-dimensional signals is performed to compute principal components of variation of the multi-dimensional signals. Features extracted from the principal components are used in detecting physiological events.

17 Claims, 9 Drawing Sheets

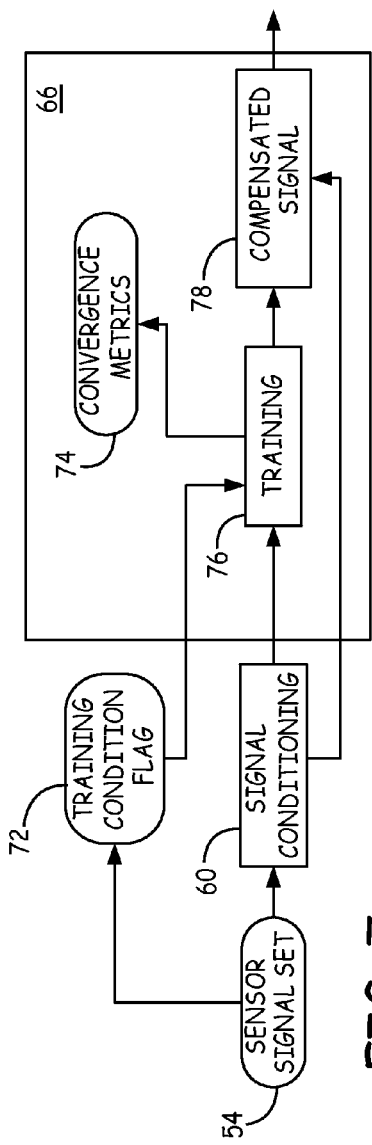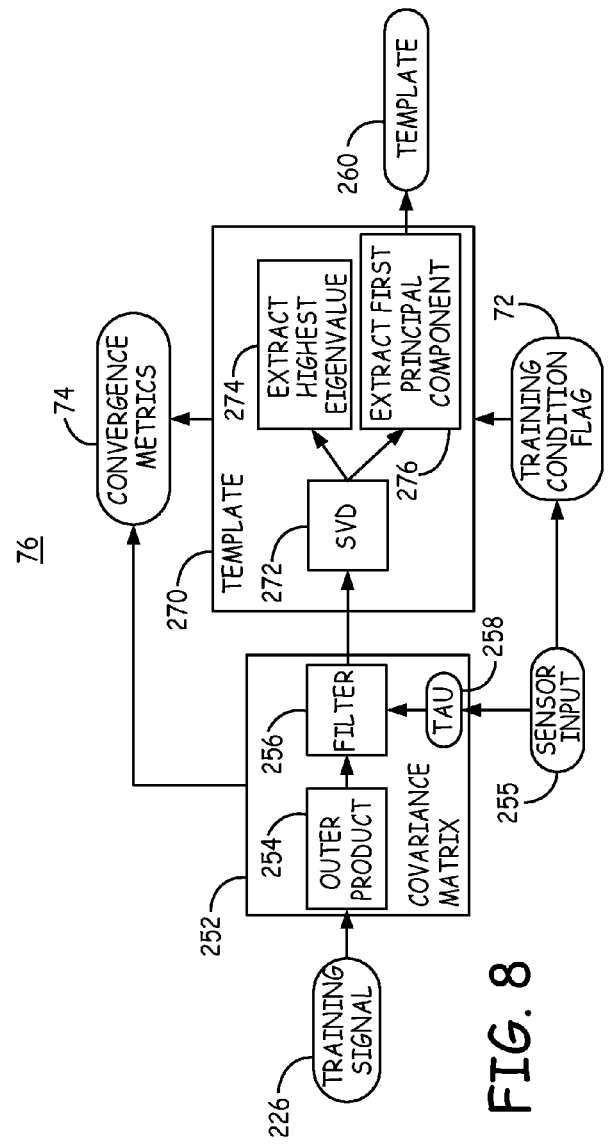

US 8,587,426 B2

IMPLANTABLE MEDICAL DEVICE WITH ADAPTIVE SIGNAL PROCESSING AND ARTIFACT CANCELLATION

REFERENCE TO RELATED APPLICATIONS

The present non-provisional U.S. patent application claims the benefit of U.S. Patent Application 61/144,943, filed provisionally on Jan. 15, 2008, and entitled "IMPLANTABLE MEDICAL DEVICE WITH ADAPTIVE SIGNAL PROCESSING AND ARTIFACT CANCELLATION", incorporated by herein by reference in it's entirety.

TECHNICAL FIELD

The disclosure relates generally to medical devices and, in particular, to a medical device and associated method for processing sensor signals.

BACKGROUND

Implantable medical devices (IMDs) used to monitor physiological conditions or to deliver therapy typically include one or more physiological sensors. Examples of IMDs include hemodynamic monitors, pacemakers, implantable cardioverter defibrillators (ICDs), myostimulators, neurological stimulators, drug delivery devices, insulin pumps, glucose monitors, etc. The physiological sensors used in conjunction with IMDs supply time-varying signals that are related to a physiological condition from which a patient's physiological or pathological state or a need for therapy can be assessed.

Chronically implanted sensors function in an environment with changing artifact and signal characteristics, as well as serious power constraints. In order to provide the most effective therapy or accurate diagnosis, it is important to identify, from the physiological signals produced by sensors, which signal or signals contains desired information regarding the physiological condition being monitored. It is also important to cancel or reduce the effects of artifacts within the sensor signals. This can be challenging in the use of chronically implanted physiological sensors, which can sense multiple sensor signals each having differing signal responses under differing patient conditions.

BRIEF DESCRIPTION OF THE DRAWINGS

FIG. 7 is a functional block diagram of a PCA processing module according to one embodiment.

FIG. 8 is a functional block diagram of a training module included in the PCA module for computing principal component templates from a multi-dimensional signal.

DETAILED DESCRIPTION

Figure 1:
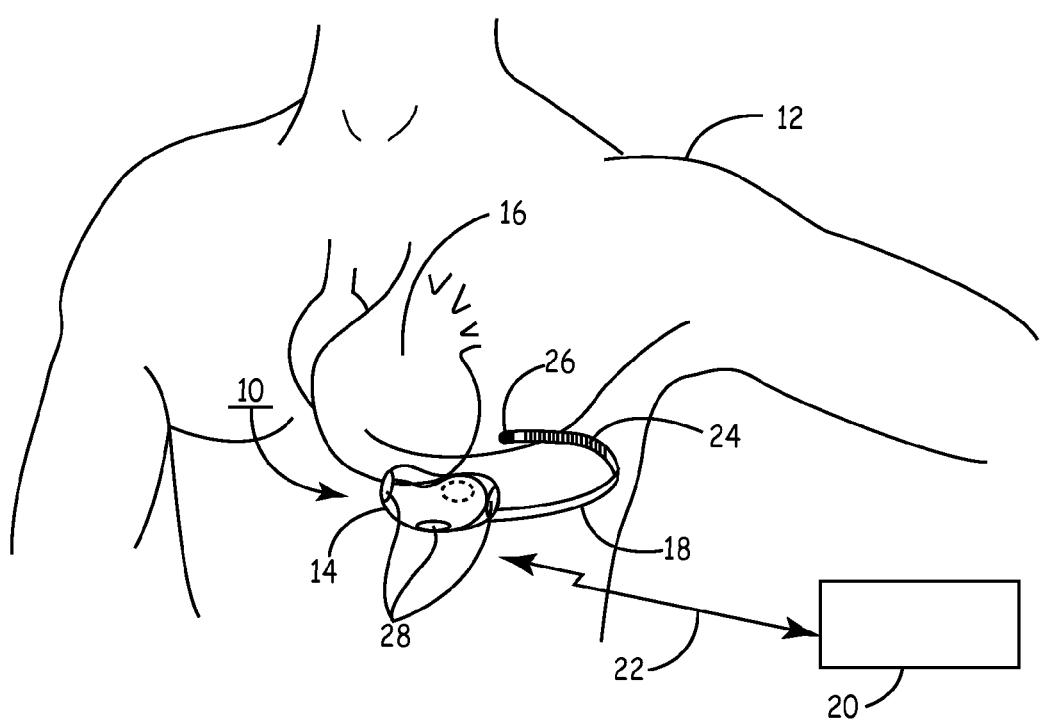
FIG. 1 is an illustration of one embodiment of an IMD in which signal processing methods described herein may be implemented.

In the following description, references are made to illustrative embodiments. It is understood that other embodiments may be utilized without departing from the scope of the disclosure. For purposes of clarity, the same reference numbers may in some instances be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

As used herein, a "multi-dimensional signal" is any signal comprising multiple signal components or "dimensions" which may be separated, for example, in time, frequency, space or by sensor type. Sensor types may include, but are not limited to, electrical sensors (e.g. electrodes), physical sensors (e.g., pressure transducers, motion transducers, acoustical sensors, etc.), optical sensors, and chemical sensors (e.g., pH sensors, glucose sensors, etc.). In one example, a multi-dimensional signal, also referred to herein as an "n-dimensional signal," includes n different signal frequencies, such as a multi-wavelength optical signal or a multi-wavelength acoustical signal. In another example, an n-dimensional signal may be an ECG signal including n different sensing electrode vectors used to acquire the ECG signal. A posture sensor, such as a three-dimensional accelerometer, may produce a three dimensional signal corresponding to patient posture or movement in x-, y-, and z-directions. A motion sensor detecting heart wall motion may detect heart motion in x-, y- and z-directions. In still other embodiments, an n-dimensional signal may include multiple signals acquired from different sensor types.

Each dimension of a multi-dimensional signal can be used to define an axis in an n-dimensional coordinate system such that a digitized, time-varying, multi-dimensional signal can be plotted in the coordinate system, allowing observation of the signal variation in each dimension. A multi-dimensional signal may be a signal acquired from a single sensor but separable into multiple dimensions. Examples of a single sensor producing a signal separable into multiple dimensions include an optical sensor detecting multiple light wavelengths or an acoustical sensor detecting multiple sound frequencies. Alternatively, a multi-dimensional signal may be multiple signals acquired from more than one sensor with each sensor signal defining a dimension in a coordinate system in which the n-dimensional signal can be plotted. For example, an EGM/ECG signal, a blood pressure signal and an oxygen saturation signal may be plotted in 3-dimensional space by plotting each signal along a respective one of the x-, y-, and z-axes of the 3D space.

As used herein, the term "variable" is used to refer to any physiological or non-physiological phenomenon that influences the multi-dimensional signal by causing a response or change in the signal as the variable changes over time. A variable that influences the multi-dimensional signal and is of interest for detecting a patient condition is referred to herein as a "variable of interest". Other variables that influence the multi-dimensional signal but are not of direct interest for detecting the patient condition are referred to herein as "artifacts". In other words, unwanted signals that significantly influence the variation of the multi-dimensional signal are considered "artifact". As will be described herein, in some cases artifact may be removed or suppressed from the multi-dimensional signal using principal component analysis (PCA). Signals that do not contribute to a principal component of variation of a multi-dimensional signal are referred to herein as "extraneous" signals and can be eliminated from the multi-dimensional signal.

FIG. 1 is an illustration of one embodiment of an IMD in which signal processing methods described herein may be implemented. IMD 10 is shown embodied as a subcutaneous ICD used to monitor the heart 16 of patient 12 and deliver electrical stimulation therapies as needed. IMD 10 is merely one example of a medical device which may acquire a multi-dimensional signal. It is recognized the signal processing and analysis methods described herein may be implemented in any medical device, including implantable and external medical devices, which employ one or more physiological sensors that generate a physiological signal having multiple signal dimensions. As described above, different signal dimensions may relate to different signal frequencies, different sensor positions within the body, different operating frequencies of the sensor or sensors, or other signal aspects separable according to time, frequency, space or sensor type.

The term "physiological sensor" as used herein refers to any sensor, such as an electrode or transducer, that is responsive to a physiological phenomenon and generates a signal correlated to the physiological phenomenon. Such sensors may be responsive to electrical, chemical or mechanical phenomenon. Examples of physiological sensors include, but are not limited to, electrodes, optical sensors, pressure sensors, acoustic sensors, pH or other blood chemistry sensors, motion sensors such as accelerometers and MEMs-based sensors.

In the example of FIG. 1, IMD 10 includes an optical sensor 30. Optical sensor 30 is shown incorporated along the housing 14 of IMD 10. For example optical sensor components such as light emitters, light detectors and sensor electronics, may be located within housing 14 adjacent a window formed in housing 14 to allow light signals to be emitted and received by sensor 30. IMD 10 is implanted in a posterior, subcutaneous position. Sensor 30 may be positioned along housing 14 such that sensor 30 faces centrally, toward muscle tissue beneath IMD 10. Other arrangements of an optical sensor in an IMD system are possible, including arrangements in which an optical sensor is carried by a lead extending from IMD 10.

IMD 10 includes housing 14 for enclosing IMD circuitry. A connector (not explicitly shown in the view of FIG. 1) is provided along housing 14 for electrically coupling a subcutaneous sensing and cardioversion/defibrillation therapy delivery lead 18 to circuitry enclosed by housing 14.

Subcutaneous lead 18 includes of a distal defibrillation coil electrode 24 and a distal sensing electrode 26 and a proximal connector pin (not shown) for connection to IMD 10 via the IMD connector. IMD 10 further includes multiple electrodes 28, incorporated along housing 14. Electrodes 28 are positioned along the periphery of the housing 14 and connected via feedthroughs to electronic circuitry within housing 14. Electrodes 28 shown in FIG. 1 may be positioned to form orthogonal signal vectors though other embodiments may include any number of subcutaneous housing-based electrodes. Any of the electrodes 28, sensing electrode 26, and coil electrode 24 may be selected in any combination for sensing subcutaneous ECG signals for use in monitoring a patient's heart rhythm and timing the delivery of anti-arrhythmia therapies.

ECG signals sensed by IMD 10 can be used for detecting cardiac arrhythmias such as ventricular tachycardia (VT) and ventricular fibrillation (VF). Optical sensor 30 generates a time-varying optical signal that varies in response to changes in the perfusion of a volume of tissue adjacent to sensor 30. The optical sensor signal may be used by IMD 10 in detecting or confirming a patient condition, such as VT or VF, which would cause a change in local tissue perfusion adjacent sensor 30.

A reflectance signal measured using optical sensor 30 will be influenced by multiple variables. For example, pulsatility of blood flow through the tissue is one variable that influences each wavelength (i.e., dimension) of a multiple-wavelength signal. Each wavelength may be influenced in varying degrees by the blood flow pulsatility. A pulsatile or alternating current (AC) signal response to the pulsatility of blood flow through the tissue will be present during normal sinus heart rhythm. The optical signal response will change with changing heart rhythms.

A reflectance at a given wavelength measured by optical sensor 30 may also vary with respiration, patient body motion, tissue encapsulation or other changes in tissue composition in the vicinity of sensor 30 and other possible variables. Each of these variables may produce different signal responses in the multi-wavelength sensor signal. As such, each wavelength of detected light will include different information relating to a variable of interest, e.g. blood flow pulsatility, and all other variables influencing the signal. As indicated previously, variables influencing the multi-dimensional signal which are unwanted for detecting a particular patient state or condition can be referred to as "artifact". For example, for the purposes of detecting a cardiac rhythm, the blood flow pulsatility may be the variable of interest while other variables that influence the multi-dimensional signal can be considered to be artifact, e.g. respiration, body motion, patient posture, tissue composition changes, and so on.

In stating that artifacts are not variables of interest is not to say that these variables do not change with a particular patient state or condition being detected but merely that these variables are not the primary variable relied upon in a particular algorithm designed to detect a particular patient state. For example, the blood flow pulsatility may be a variable of interest for detecting VF, yet patient position, activity, and respiration may change in the presence of VF, perhaps even in a predictable manner. These variables, however, are secondary variables which are not direct indicators of VF and can change as the result of other patient conditions not related to changes in heart rhythm.

In various embodiments, one or more variables may be variables of interest for detecting a patient state and one or more variables may be considered artifacts. As will be described herein, signal processing methods can use Principal Component Analysis (PCA) to evaluate the principal components of variation of a multi-dimensional signal in response to differing conditions. These signal processing methods allow the analysis of multi-dimensional signal response to the variable(s) of interest and suppression of artifact. Extraneous signals not significantly influencing the multi-dimensional signals can be removed. Furthermore, as will be described, a variable that is considered artifact under some conditions or for some portions of a detection algorithm may be a variable of interest under other conditions or for other portions of a detection algorithm.

The signal processing methods described herein may be implemented in IMD 10 for analyzing a multi-wavelength signal from optical sensor 30. In other embodiments, the signal processing methods may be performed to analyze a multi-vector ECG signal sensed by IMD 10, e.g. using two or more sensing vectors acquired by electrodes 24, 26 and 28. It is recognized that other medical devices may include other sensors, carried by a lead extending from an IMD, incorporated in or on an IMD, or as a separate sensing device. Any multi-dimensional signal acquired by a medical device may be processed and analyzed utilizing PCA methods as described below.

IMD 10 includes telemetry circuitry (not shown in FIG. 1) enabled for bi-directional communication with an external device 20 via a telemetry link 22. External device 20 may be a programmer, home monitor, or another medical monitoring or therapy delivery device. Signal processing and analysis methods may be fully implemented in IMD 10 or across multiple medical devices. In one embodiment, signal processing and analysis is fully implemented in IMD 10 and resulting data made available to a clinician by transmitting data from IMD 10 to external device 20. In alternative embodiments, n-dimensional signal data may be acquired by IMD 10 and transferred to external device 20 with portions of the signal processing and analysis methods implemented in external device 20.

IMD 10 is an illustrative example of one medical device capable of receiving multiple physiological signals that can be grouped into multiple multi-dimensional signals. Methods described herein may be embodied in numerous implantable and/or external medical device systems which are capable of acquiring multiple sensor signals for monitoring a patient. The examples provided in conjunction with FIG. 1 and FIG. 2 provided herein are merely illustrative and not intended to limit the application of the multi-dimensional signal processing and analysis methods described herein.

Figure 2:
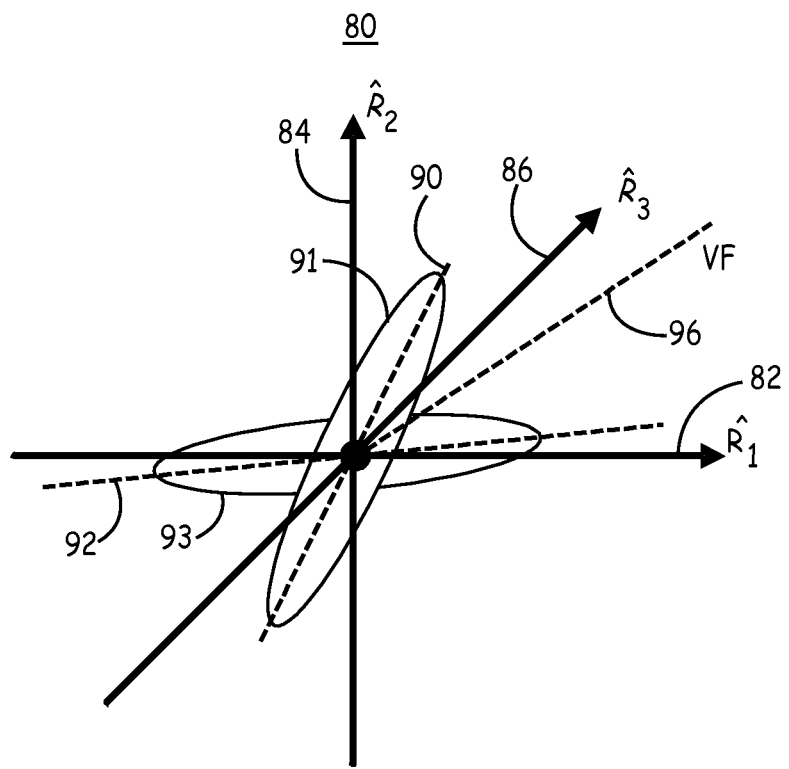
FIG. 2 is a diagram illustrating concepts of PCA applied to a multi-dimensional signal.

FIG. 2 is a diagram illustrating concepts of PCA applied to a multi-dimensional signal. PCA is a linear transformation of data to an n-dimensional coordinate system. In the illustrative example of FIG. 2, a three-dimensional coordinate system 80 is defined for a three-dimensional sensor signal. In this example, a three-wavelength optical sensor signal is used to illustrate the concept of an n-dimensional signal and coordinate system, however, it is recognized that any multi-dimensional signal can be processed using the methods described herein.

The three-wavelength optical signal can be plotted in the three-dimensions of system 80. Values for reflectance measurements for a first wavelength, R1, are plotted relative to the x-axis 82. Values for reflectance measurements for a second wavelength, R2, are plotted relative to the y-axis 84, and reflectance measurements for a third wavelength, R3, are plotted relative to the z-axis 86.

As will be described herein, a principal component of variation of the multi-dimensional signal under known conditions can be determined using PCA. In PCA, the greatest variance of the data along a projection in the n-dimensional coordinate system is defined to lie along an axis referred to as the "first principal component". The second greatest variance of the data defines a second axis, and so on. PCA can be used to efficiently model multi-dimensional data using fewer dimensions. In practice, the first principal component of the signal data is determined under known conditions and stored as a template to reflect the greatest variance of the multi-dimensional signal under the known conditions. Other principal components associated with smaller variation can be ignored in some embodiments such that the multi-dimensional signal is reduced to a single dimension along the first principal component. Signals not contributing to variation of the first principal component would be considered extraneous and could be disabled.

For example, as shown in FIG. 2, during normal sinus rhythm, a known condition for a cardiac pulsatility variable, the multi-wavelength reflectance signal points fall primarily within a region 91 with the greatest variation occurring primarily along an axis 90. Axis 90 can be identified as the first principal component of the three-dimensional reflectance signal data using PCA, as will be described in detail herein. Likewise, a known condition for a body motion variable, for example walking, may produce signal data falling primarily within a region 93 characterized by a first principal component defined by axis 92. The first principal component represented by axis 92 for the known condition for the body motion variable is distinct from the cardiac pulsatility variable first principal component axis 90 during normal sinus rhythm at rest. During VF, the first principal component of the three-dimensional reflectance signal may be represented by yet another unique axis 96. As such, using PCA, a principal axis representing the greatest variation of the multi-dimensional signal data can be determined under different known conditions.

The second and third principal component directions of the signal data may also be determined for each known condition. These components are not drawn in FIG. 2 for the sake of clarity; however these components may be orthogonal to the first principal component axis. These orthogonal principal components would represent the axis along which the second greatest and the third greatest variation of the data occurs for the given conditions.

A monitored multi-dimensional signal can be analyzed using one or more principal component(s) of the multi-dimensional signal determined under known conditions to detect the patient state based on the monitoring signal. For example, if a monitoring signal deviates from the principal component 90 for normal sinus rhythm and toward a VF principal component 96, a VF detection may be made or confirmed. Variation of the multi-dimensional signal due to artifact may be cancelled using the principal components of the artifact determined under known conditions. The use of PCA for canceling artifact in a multi-dimensional signal will be described in greater detail below. Briefly, if body motion is considered an artifact and is contributing to the variation along the first principal component axis of a monitoring signal, the contribution could be suppressed by using a template of the first principal component 92 stored for the body motion condition.

By using principal components, an n-dimensional signal can be reduced to fewer dimensions, e.g. a 1-dimensional signal, which retains significant variation associated with a variable of interest. The reduced-dimensional signal enables simpler detection algorithms to be performed than algorithms which evaluate all of the dimensions of the original multi-dimensional signal. Retaining the greatest variation of the original signal in the reduced-dimensional signal promotes accurate detection of a corresponding patient event or condition.

In the illustrative example of FIG. 2, changes in the pattern of a three-dimensional optical sensor signal due to changes in a cardiac condition and artifact (in this example motion due to walking) are shown. The concept of plotting a multi-dimensional signal in n-dimensional space, however, for observing patterns in the data that represent a physiological condition of the patient may be applied to any sensed physiological signals. By plotting the multi-dimensional signal in an n-dimensional space, trends of the data which represent a change in a physiological condition may be observed. The change in the physiological condition may be a non-pathological or pathological change. A distinct physiologic state, whether normal or pathological, can be plotted in n-dimensional space using a multi-dimensional signal and, in this way, be mathematically separable from other physiologic states. A clinician may be able to observe patterns in the plotted multi-dimensional signal data for patient diagnosis and prognosis. Patterns in the plotted multi-dimensional signal data may further provide useful information in overall patient management, e.g. managing pharmacological therapies, dietary recommendations, exercise or activity recommendations, and medical device-delivered therapies.

Patterns in the plotted multi-dimensional signal data may be more readily observed to be indicative of a particular physiological condition than when parallel observation or analysis of individual signals (dimensions) of a multi-dimensional signal is performed. For example, once the primary component of three-dimensional optical sensor signal data is known for different physiological conditions, such as different cardiac conditions, activity conditions, and respiration conditions, the first principal component axes representing those conditions can be plotted in an n-dimensional space. Patient data may then be plotted in the n-dimensional space as it is acquired.

Patterns of the data trending toward any of the plotted first principal component axes, or variation of the data occurring primarily along a principal component axis, is evidence of the physiological condition corresponding to that axis. In the example of FIG. 2, optical sensor signal data from a patient may be acquired during unknown conditions and plotted in the three dimensional coordinate system 80 shown in FIG. 2. As variation in the plotted signal data occurs along any one of the principal component axes 90, 92 or 96, the physiological state of the patient can be determined as corresponding to the condition represented by that principal component axis.

Figure 3:
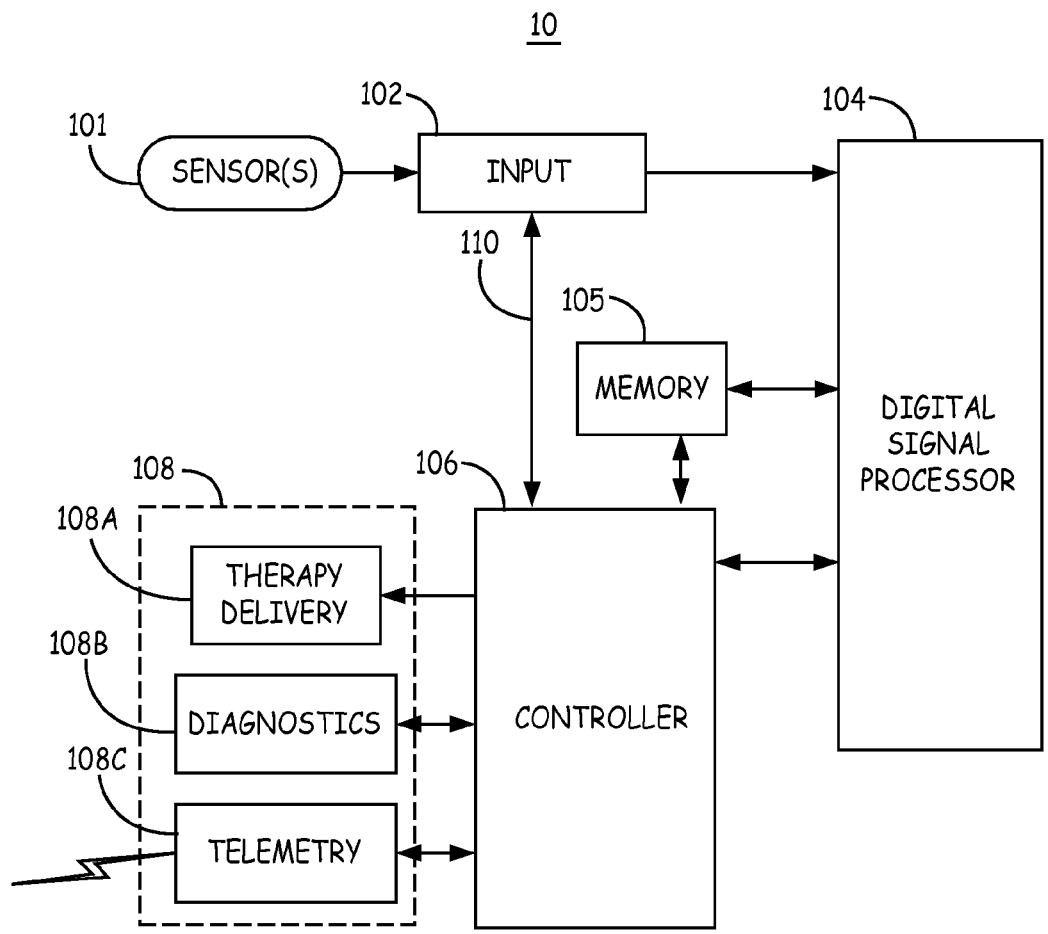
FIG. 3 is a functional block diagram of the IMD shown in FIG. 1.

FIG. 3 is a functional block diagram of IMD 10. IMD 10 includes a sensor module 101 including at least one physiological sensor, input module 102, digital signal processor (DSP) 104, memory 105, controller 106, and output module 108. Sensor module 101 may be a single sensor or any combination of sensors generating one or more n-dimensional signals responsive to physiological variables. Sensor module 101 may include an optical sensor 30 as described above generating an n-wavelength optical signal. Sensor module 101 may include additional sensors used by IMD 10 for detecting variable conditions and for use in detecting patient conditions and making therapy delivery decisions. Sensor module 101 may include an activity sensor, a posture sensor, ECG/EGM electrodes or other physiological sensors listed previously.

Input module 102 acquires sensor signal(s) when enabled for sensing by controller 106 by control/status line 110. Input module 102 may perform pre-processing signal conditioning, such as analog filtering. Input module 102 provides an n-dimensional signal to DSP 104. Input module 102 may additionally provide other sensor signals being evaluated individually to DSP 104 and/or controller 106 for use in monitoring variable conditions and detecting a patient state.

DSP 104 receives the n-dimensional sensor signal and performs adaptive processing to provide a signal having a reduced dimensionality that can be used by controller 106 to monitor a patient condition and appropriately control output module 108. For an n-dimensional signal, up to n−1 dimensions can be eliminated based on PCA to allow the sensed signal response to a variable of interest to be analyzed for efficient and accurate detection of a patient condition. The adaptive processing performed by DSP 104, which includes PCA, computes the principal components of the n-dimensional signal variation under known conditions. PCA may be performed to compute the principal components of the signal data in response to one or more known conditions relating to a variable of interest. PCA may additionally or alternatively be performed to compute the principal components of the signal data in response to one or more known conditions for artifacts. Input from sensors 101 may be used to identify the variable conditions.

The results of PCA are stored in memory 105 and can be used to extract a signal having fewer than n dimensions but retaining significant variability of the signal response to a variable of interest for detecting a specific patient condition. This reduced dimensional signal may be obtained through artifact cancellation using principal components obtained for known conditions or by determining a match between a monitored n-dimensional signal with a first principal component template corresponding to a known condition.

Controller 106 analyzes the digitally processed signal provided by DSP 104 to detect a patient condition using a detection algorithm which applies detection criteria to the received signal or metrics derived from the signals. Controller 106 may adaptively select artifacts to cancel based on results of the PCA. Controller 106 can also use the results of the processing by DSP 104 to selectively enable or disable sensors 101, or to select physiological signals processed by DSP 104. If any signal dimension is not significantly contributing to the variation of the n-dimensional signal along a principal component, the value computed for that dimension in the principal component vector will be small or approaching zero as compared to other principal component values (e.g. a principal component axis might be defined by a vector of [x,y,~0]). The sensor or signal corresponding to a signal dimension having the smallest contribution to a principal component may be classified as an extraneous signal. A sensor providing the extraneous signal can be disabled by controller 106 or the signal can be ignored during processing by DSP 104.

The sensor/signal selection can simplify the computations performed by DSP 104, thus reducing energy demands. In addition, the total amount of energy consumed is reduced by turning off those sensors that are providing extraneous signals, signals high in artifact or signals that are merely redundant to signals received from other sensors.

The ability to adapt digital signal processing and the selection of sensor signals (and sensors) over time allows IMD 10 to accommodate situations in which artifact and signal characteristics change over time. By periodically repeating signal processing operations, DSP 104 provides data from which controller 106 can select signals or sensors to be used to thereby eliminate extraneous sensor signals and suppress artifact.

Controller 106 uses the digitally processed signals to make decisions regarding therapy delivery by therapy delivery module 108A, for storing patient data in diagnostics module 108B, and/or for transmitting data by telemetry module 108C. Controller 106 may employ a microprocessor and associated memory or digital state machines for timing sensing and therapy delivery functions and controlling other device operations in accordance with a programmed IMD operating mode.

Therapy delivery module 108A may provide electrical stimulation therapy or drug delivery therapy. In one embodiment, therapy delivery module 108A includes a pulse generator for generating low-voltage pacing pulses, e.g. for bradycardia pacing, cardiac resynchronization therapy, and antitachycardia pacing, and/or for generating high-voltage cardioversion/defibrillation shocks. Therapy delivery unit 108A includes therapy delivery elements (not shown) such as electrodes, catheters, drug delivery ports or the like for administering a therapy.

Diagnostics module 108B is used to store data relating to the analysis of digitally processed signals. Such data may be made available to a clinician via telemetry by telemetry module 108C or accessed by controller 106 for making therapy decisions. Diagnostics module 108B may perform analysis of multi-dimensional signal data plotted in an n-dimensional space to detect variation of signal data along principal components determined for known physiological conditions. When a pathological condition is detected that warrants medical attention, the controller 106 may cause telemetry module 108C to transmit a warning or alert to an external device or to a remote patient management database. A medical device system capable of generating an alert in response to detecting a patient condition is generally disclosed in U.S. Pat. Publication No. 2006/0064136 (Wang), hereby incorporated herein by reference in its entirety. A remote patient management system is generally disclosed in U.S. Pat. No. 6,497,655 (Linberg et al.), hereby incorporated herein by reference in its entirety.

Signal data may be additionally or alternatively transmitted to an external device or remote patient management database to allow plotting and display of multi-dimensional signal data in an n-dimensional coordinate system. Principal components for known physiological conditions may be superimposed on the plotted data to allow variation of the multi-dimensional signal along axes corresponding to known conditions to be recognized. By observing particular patterns in the signal data in n-dimensional space, a clinician may be able to diagnose or predict a particular patient condition and take appropriate action.

The signal acquisition, processing and analysis methods described herein may be implemented using any combination of software, hardware, and/or firmware in a dedicated module or across multiple modules within an IMD. Furthermore signal processing and analysis methods may be implemented in a distributed manner across more than one device in a medical device system. For example, the signal acquisition may be performed by an implanted or an external device and at least a portion of the signal processing or analysis, including PCA, may be performed by another implanted or external device in telemetric communication with the signal acquisition device.

Figure 4:
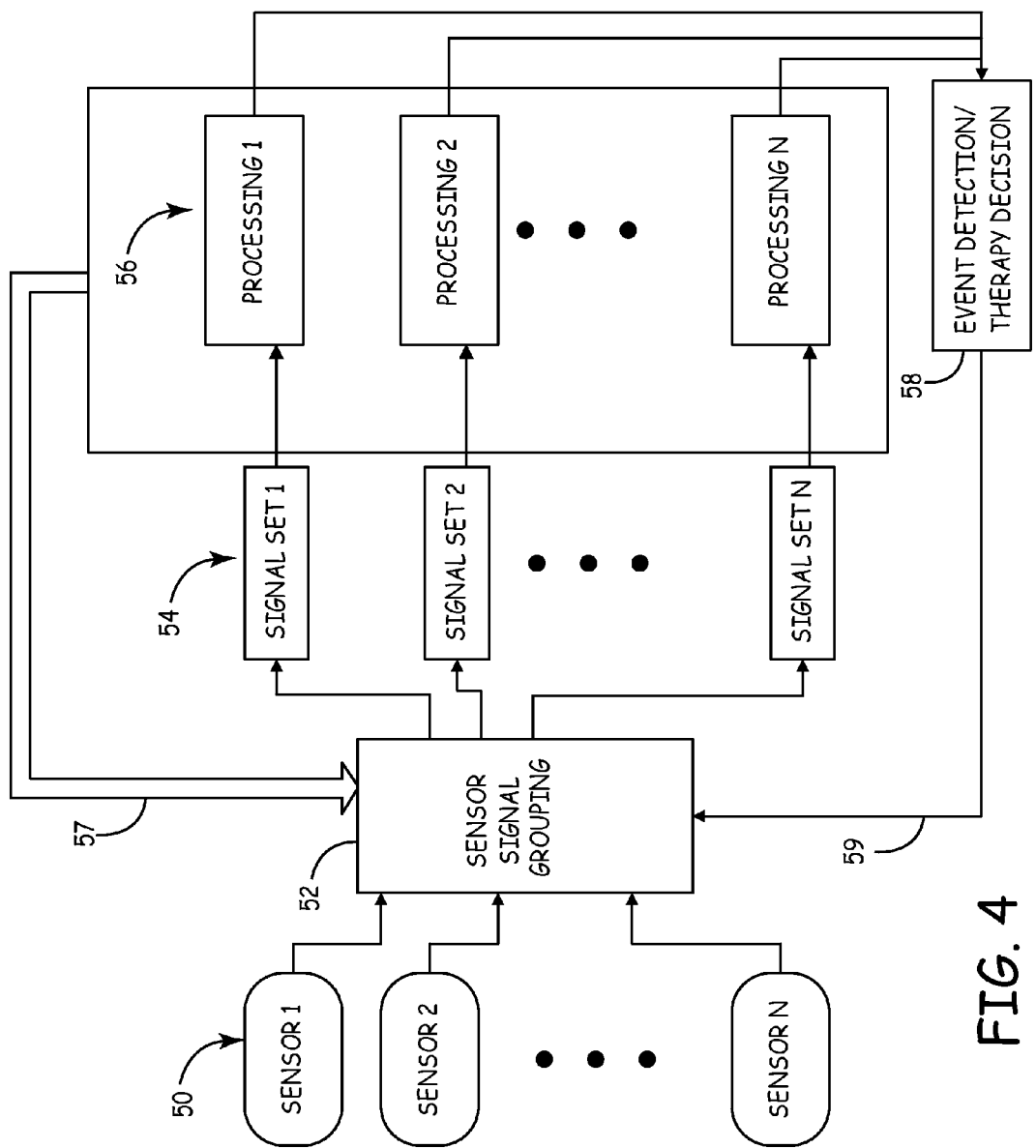
FIG. 4 is a functional block diagram of a set of physiological sensors combined into multiple signal sets for processing multiple, multi-dimensional signals.

FIG. 4 is a functional block diagram of a set of physiological sensors combined into multiple signal sets for processing multiple, multi-dimensional signals. Multiple sensors 50 provide input to a sensor signal grouping block 52. Grouping block 52 groups the sensor signals into multiple sets of sensor signals 54, each received by a respective processing block 56, as a multi-dimensional signal. Each set of sensor signals 54 is grouped to provide a unique multi-dimensional signal, which may have two, three or more dimensions. Each processing block 56 determines features from the sensor signal set. At least some of the features determined by processing modules 56 are extracted after performing PCA on the sensor signal set to compute a compensated signal. A "compensated signal" is a signal of reduced dimensionality determined using PCA. The compensated signal is the signal obtained after performing PCA on the multi-dimensional signal to remove artifact and/or reduce the dimensionality of the multi-dimensional signal to obtain a signal having the greatest variation corresponding to a variable to be evaluated for the given signal set. Some features may additionally be extracted from sensor signals prior to performing PCA, referred to herein as the "uncompensated signal".

Each processing module 56 outputs signal set features to an event detection and therapy delivery decision block 58. Any combination of uncompensated signal features and compensated signal features is analyzed in a detection algorithm for detecting a patient condition or physiological event. Based on the analysis, the medical device system may automatically make a therapy delivery decision to either start or stop therapy delivery or otherwise adjust a therapy delivered by the medical device.

The sensor signal grouping performed by block 52 may be programmable or adaptive to changing signals or event detections. The incoming sensor signals may be grouped in response to signal features determined by processing blocks 56. As such feedback signal 57 may provide sensor signal grouping block 52 signal feature data that is used by signal grouping block 52 to select the signal sets 54 provided to processors 56. In some embodiments, a compensated signal may be rejected or disabled based on the analysis of another compensated signal. For example, when a condition is present based on the analysis of one compensated signal, another signal may be known to be unreliable for detecting a patient event and is thus rejected for use in event detection as long as the condition is present.

Figure 5:
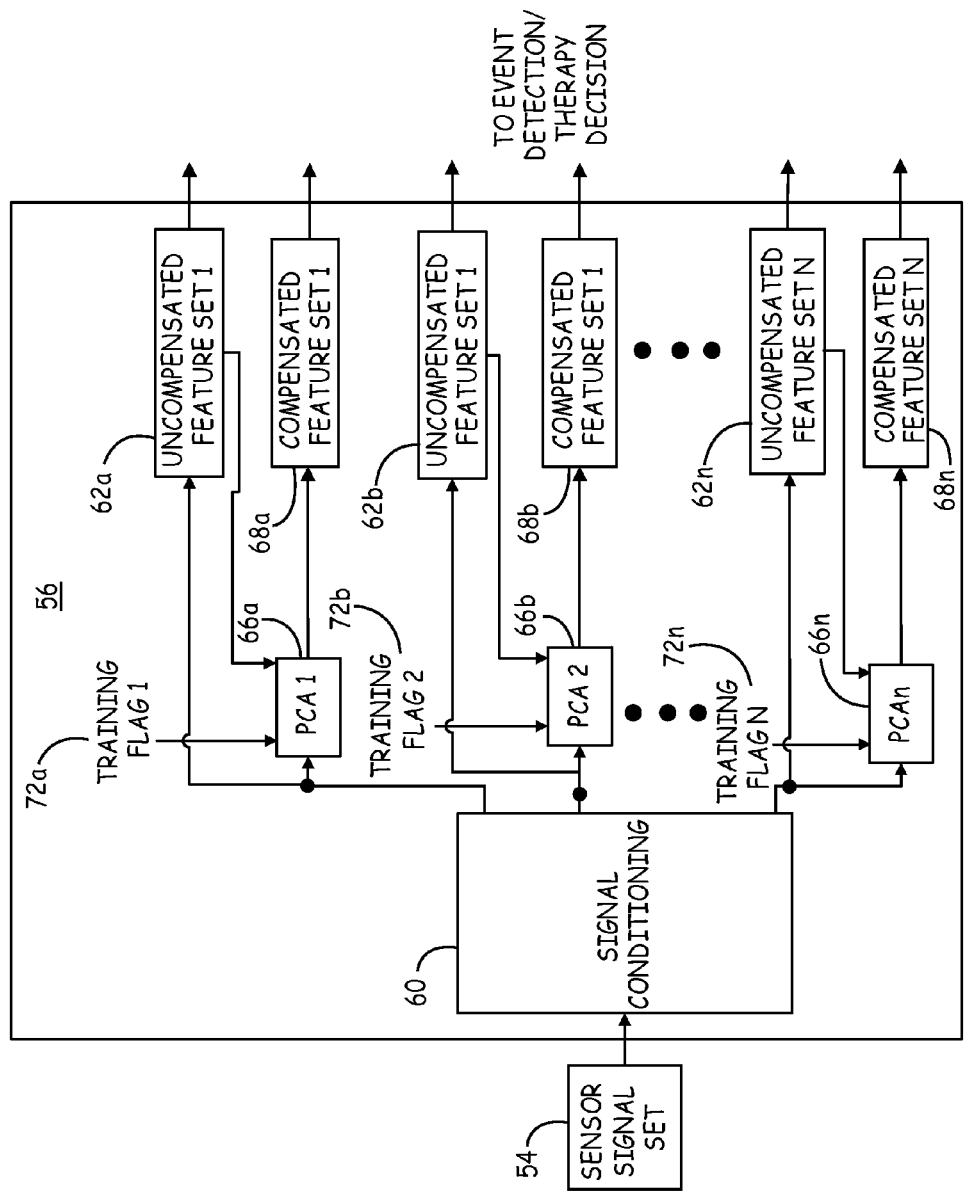
FIG. 5 is a functional block diagram of a processing module shown in FIG. 4.

Each processing module 56 receives a training flag input as will be shown and described in conjunction with FIG. 5. A training flag input (not shown in FIG. 4) indicates a known patient condition. When a known condition is flagged, the respective processing module 56 extracts signal features or templates corresponding to the known condition. The training flag status may also be provided as input to sensor signal grouping module 52 for use in selecting which sensor signals are grouped together in the signal sets 54.

Additionally or alternatively, the sensor signal grouping block 52 may be influenced by event detection or a therapy status. A feedback signal 59 from event detection/therapy decision block 58 may be used by sensor signal grouping to select which sensor signals are grouped into signal sets 54.

FIG. 5 is a functional block diagram of a processing module 56 shown in FIG. 4. Each processing module 56 receives a set of sensor signals 54 that have been grouped to form a multi-dimensional signal. The set of sensor signals may be received from a single sensor, such as multiple wavelengths from an optical sensor, multiple frequencies from an acoustical sensor, or multiple axes from an accelerometer. Alternatively, a sensor signal set is a combination of signals from different sensors.

Signal conditioning block 60 is provided for receiving a set of sensor signals from the signal grouping module and performing any filtering, rectification, or other signal conditioning needed before deriving signal features used for event detection. For example, the sensor signal set may be filtered for low or high frequency noise that is non-physiological. Computation of average signals, time derivatives of signals, or other signal conditioning may be performed.

Uncompensated feature extraction blocks 62a through 62n, collectively referred to by reference numeral "62", are processing modules that receive the set of conditioned signals from signal conditioning module 60. Uncompensated feature extraction blocks 62 each derive different sets of signal features directly from the conditioned signals. The output from each of the uncompensated feature extraction blocks 62 are provided as input to an event detection algorithm (block 58 of FIG. 4). Each uncompensated feature set computed by blocks 62 may include one or more features derived from the input signal set. The feature(s) may be derived using any combination of the signals included in the signal set.

PCA blocks 66a through 66n, collectively "66", are processing modules for computing a compensated signal from the sensor signal set received from signal conditioning block 60. The compensated signal may be computed to remove the variation of the multi-dimensional signal in a dimension associated with an artifact condition. Alternatively, variation along a first principal component is selected as the variation of interest and other principal component vectors are removed from the multi-dimensional signal to obtain a one-dimensional compensated signal.

It is recognized that variation of the multi-dimensional signal treated as artifact by one PCA block 66 may be treated as a variable of interest by another PCA block 66. Referring again to the previous example, variation of the multi-dimensional signal associated with patient motion may be treated as artifact by a PCA block 66 that is determining a compensated signal having its first principal component corresponding to cardiac pulsatility while another PCA block 66 may determine a principal component having its greatest variation corresponding to patient motion in order to assess the influence of patient motion on other signal dimensions. The different compensated signals produced by the different PCA blocks 66 may thus be used to select sensor signal sets, extracted features, and/or detection algorithms used for detecting a patient condition based on the features of the different compensated signals.

Compensated feature extraction blocks 68a through 68n, collectively "68", each extract a unique set of features from the compensated signals received from respective PCA blocks 66. The compensated features extracted and provided as output from processing module 56 are received by an event detection/therapy decision block for detecting patient conditions or events. The feature sets derived by blocks 62 directly from the conditioned multi-dimensional signal prior to performing PCA can be referred to as "uncompensated feature sets". The compensated feature sets derived by blocks 68 after PCA may include features analogous to the uncompensated feature sets or may be entirely different features.

In some embodiments, uncompensated feature sets are provided as input to the PCA blocks 66 for controlling when to perform PCA to obtain a compensated signal. For example, when any of the feature sets extracted from the uncompensated signals represent a high degree of variability due to artifact, out of range values, produce confounding results by event detection block 58 (FIG. 4) or otherwise make event detection uncertain or inconclusive, PCA may be invoked to allow analysis of compensated signals for use in event detection. While output from each uncompensated feature block 62 is shown to provide feedback to a particular PCA block 66, it is recognized that feedback for controlling operation of PCA blocks 66 may be provided by any combination of the feature sets computed by uncompensated feature extraction blocks 62.

Furthermore, a compensated feature set computed by compensated feature set extraction blocks 68 may be used as feedback for controlling when another compensated signal is determined by a particular PCA block 66. While not explicitly shown in FIG. 4 for the sake of clarity, feedback from any of the uncompensated feature extraction blocks 62 and/or compensated feature extraction blocks 68 may be used to "turn on" or "turn off" other PCA blocks 66, uncompensated feature extraction blocks 62, or compensated feature extraction blocks 68. In this way, minimal signal processing and analysis can be performed until the processor determines that additional analysis is needed for detecting patient events or conditions. The need for additional signal analysis may be based on any feature set resulting in unreliable or confounding results or when a known condition exists. Additional signal analysis may alternatively be triggered when analysis of a monitored feature set indicates that a patient event is predicted or expected. Additional compensated and/or uncompensated feature extraction and analysis is triggered to monitor for the expected event.

Some of PCA blocks 66 may compute a compensated signal by isolating the first principal component of what may be considered artifact in other PCA blocks to determine the presence of a patient condition, such as a patient posture, patient motion or patient activity, that is considered to be a potential source of signal artifact influencing a variable of interest. For example, if a multi-dimensional signal arising from the selected sensor set includes an accelerometer signal, an ECG signal and a blood pressure signal, PCA may be performed to extract a one-dimensional signal along the first principal component of the multi-dimensional signal during a known patient activity level to obtain a one-dimensional signal representative of that activity. Computation of the one-dimensional signal during unknown activity can be used to detect the patient activity condition. Knowing the patient activity condition, the IMD can make decisions about other sensor set groupings and/or which compensated signals and feature sets to compute.

Another of the compensated feature extraction blocks 66 may be used to extract a one-dimensional signal along the first principal component of the multi-dimensional signal variation corresponding to an event of interest, such as a cardiac event. As such, in detecting an event of interest, a number of compensated and uncompensated signal feature sets may be determined from each sensor signal set for detecting the event of interest as well as related patient conditions or events that may be secondary conditions related to the primary event of interest or artifact conditions. The secondary or artifact events or conditions may be used in selected which feature set(s) are relied on for detecting the primary event of interest.

For example, the presence of detected patient activity based on the one compensated feature set can be used to negate a cardiac event detection based on another compensated feature set or to require additional data analysis before confirming a detected cardiac event. In other words, different sets of compensated features can be computed from different compensated signals derived from a single sensor set 54 using different PCA blocks 66.

Multiple uncompensated feature sets and compensated feature sets may be derived from each signal set 54. Multiple uncompensated feature sets and multiple compensated feature sets may be extracted from the same uncompensated and compensated signals, respectively, over different intervals of time or over different frequency bandwidths of the multi-dimensional signal. For example, in detecting a cardiac condition or event, a sensor set input to signal conditioning block 60 may include multiple frequency bands of an acoustical sensor. Compensated and uncompensated feature sets may be extracted from the multi-dimensional signal across different time intervals of the signal. For example, in cardiac applications, an uncompensated feature set and/or a compensated feature set may be derived from the multi-dimensional signal from time intervals corresponding to the first heart sound, time intervals corresponding to the second heart sound, and so on. These multiple sets of features selected from the same multi-dimensional signal but at different time intervals can be used to corroborate an event detection, e.g. a cardiac event detection based on various heart sounds.

While embodiments described herein illustrate the use of a compensated signal, i.e. a reduced dimensionality signal, for extracting signal features after performing PCA, it is recognized that a set of signal features extracted after performing PCA may be derived from a signal having the same number of dimensions as the multi-dimensional signal. PCA performed to determine the principal components of variation of the multi-dimensional signal may result in significant or meaningful variation in the same number of dimensions as the original multi-dimensional signal. As such, in some cases, features derived after performing PCA may be from a signal having an equal number of dimensions to the original multi-dimensional signal, however the orthogonal axes of variation of those dimensions will be defined by the PCA. Extraction of a set of signal features from a signal after performing PCA, therefore, is not limited to extraction from a "compensated" signal having reduced dimensionality as compared to the original multi-dimensional signal.

In some embodiments, sensor set processing block 56 operates in a training mode during training intervals of time identified by training flags 72a through 72n, collectively "72". When a training flag 72 is present indicating known conditions, the respective PCA module 66 is enabled to perform feature extraction to determine and store a template or feature set of the compensated signal for the known condition identified by the training flag 72.

When a training flag 72 is not present, sensor set processing block 56 operates in a monitoring mode for detecting patient events. During monitoring, one or more stored principal component templates determined during training may be used by PCA blocks 66 to convert the conditioned sensor set signal to a compensated signal, as will be further described below.

Figure 6:
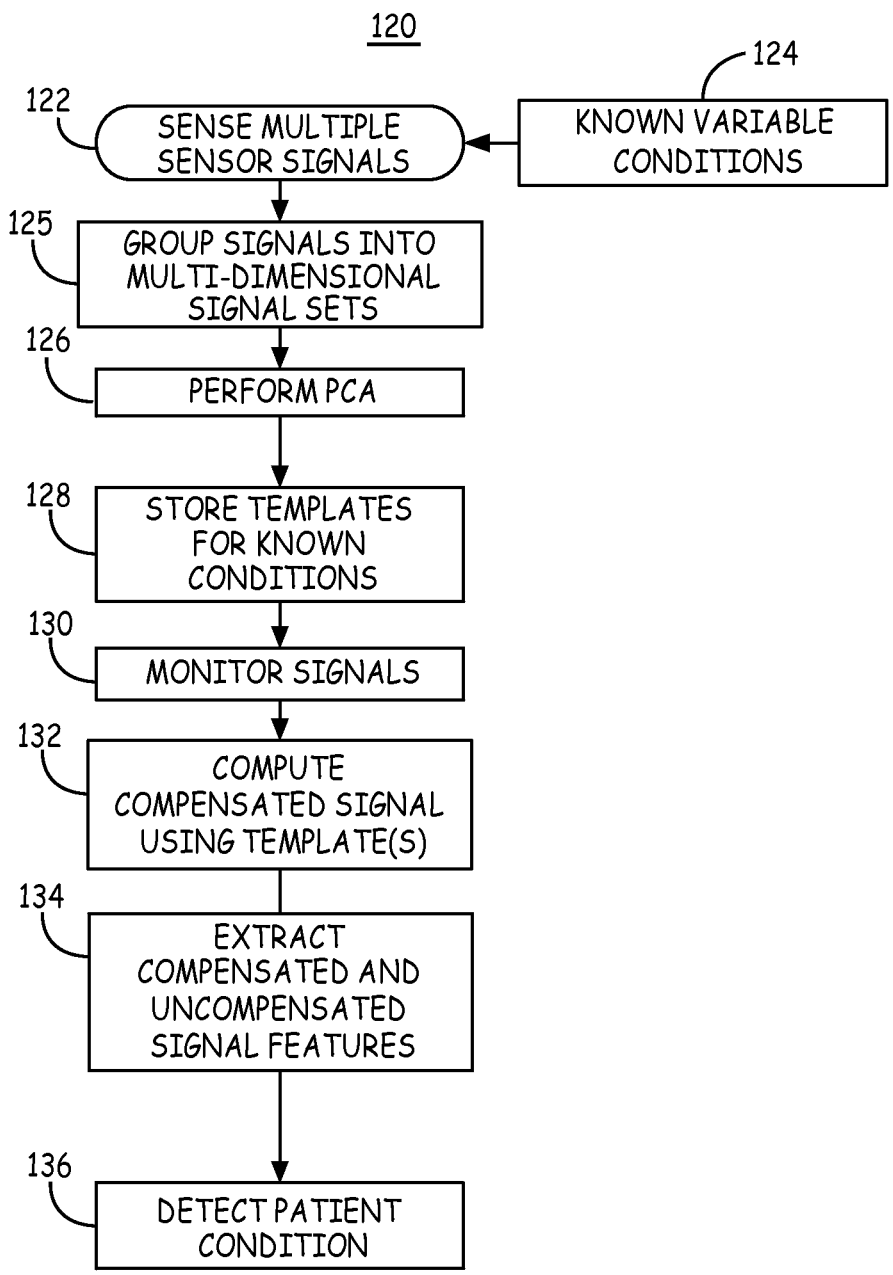
FIG. 6 is a flow chart of a method for detecting a patient condition using multiple multi-dimensional physiological signals.

FIG. 6 is a flow chart of a method 120 for detecting a patient condition using multiple multi-dimensional physiological signals. Flow chart 120 is intended to illustrate the functional operation of a medical device system, and should not be construed as reflective of a specific form of software, firmware or hardware necessary to practice the methods described. It is believed that the particular form of software, firmware or hardware will be determined primarily by the particular system architecture employed in the medical device system and by the particular sensing and therapy delivery methodologies employed by the medical device. Providing software, firmware and/or hardware to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 122, multiple multi-dimensional signals are sensed under known conditions (block 124), as indicated by a training flag. Multiple signals are acquired from physiological sensors coupled to the IMD and grouped into multi-dimensional signal sets at block 125. Each grouping may include output from one or more sensors. One example of multiple physiological sensor signals and sensor signal sets grouped to obtain multiple, multi-dimensional signals is shown in Table I.

TABLE I

| Sensors | Sensor Signal Sets | Feature Set Examples |
| --- | --- | --- |
| 3-wavelength Optical sensor | Optical multi-dimensional signal (e.g. a three dimensional signal defined by red, infrared and isobestic wavelengths) | Red reflectance<br>Infrared reflectance<br>Isobestic reflectance |
| 3-axis Accelerometer | Accelerometer multi-dimensional signal (e.g. a 3-dimensional signal defined by x-axis, y-axis and z-axis) | x-axis amplitude<br>y-axis amplitude<br>z-axis amplitude |
| Acoustic | Acoustic multi-dimensional signal (e.g. a two-dimensional signal defined a two different frequency bands or two different time intervals) | Time/Frequency Band A<br>Time/Frequency Band B<br>heart sound interval times<br>band energies<br>frequency shifts |
| Pressure | Pressure + Near-field ECG (e.g. a two dimensional signal defined by pressure in one dimension and ECG in second dimension) | time QRS -> max systolic<br>time QRS -> min diastolic<br>time QRS -> max dP/dt<br>time QRS -> ePAD |
| Far-field ECG | Acoustic + Near-field ECG (e.g. a three-dimensional signal defined by two different frequency bands and near field ECG) | QRS to heart sound times |
| Near-field ECG | Pressure + Acoustic (e.g. a three dimensional signal defined by pressure, and two different frequency bandwidths) | Heart sound to pressure metric times |

Different physiological sensors are listed in column one which may be included in an implantable medical devices system. The sensor signals may be grouped according to the multiple groupings listed in the middle column of Table 1 to produce multiple multi-dimensional signals. Feature sets listed in the third column are derived from uncompensated signals from the sensor signal set. PCA analysis performed on the sensor signal set will create a compensated signal from which additional features can be extracted. Features extracted from the compensated signal may be similar to the features extracted from the uncompensated signal set, but in other cases the compensated signal will be a completely different signal resulting in completely different features.

Known conditions input at block 124 may be identified using sensor signals or user input. The known conditions input at block 124 correspond to the training flags shown in FIG. 5. When the known conditions are identified a training flag is enabled such that the PCA module is operated to perform PCA for computing features or a signal template for the known conditions.

PCA is performed on at least one of the multi-dimensional signals at block 126 to generate a template of the principal components of variation of the signal for the known conditions. One or more principal components are stored as a template of the signal data for the known conditions at block 128. Blocks 122 through 128 may be performed for multiple sets of known conditions to enable storage of multiple templates. Each template may include one or more principal components containing the most significant variation(s) during the known condition.

The known conditions identified at block 124 may correspond to a condition for a variable of interest to allow a template of the n-dimensional signal response for the variable of interest to be stored. The known conditions identified at block 124 may correspond to normal or pathological states of the variable of interest. For example, if the variable of interest is cardiac rate, known conditions may correspond to normal sinus rhythm and one or more types of arrhythmias to allow templates for each type of heart rhythm to be stored. The storage of templates corresponding to a variable of interest allows features of an unknown signal to be analyzed using the stored template(s) for detecting a patient condition relating to the variable of interest.

Additionally or alternatively, the known conditions identified at block 124 may correspond to artifacts. One or more templates may be stored for known artifact conditions, such as activity, posture, or respiration, to allow the template to be used to cancel the signal response corresponding to the artifact during signal analysis performed to detect a patient condition.

The known conditions may be identified by the medical device automatically at block 124, for example using other sensor signals such as an activity sensor, a posture sensor, ECG electrodes, etc. Alternatively, the known conditions may be identified manually and a user-entered command transmitted to the IMD via telemetry may indicate the presence of the known conditions.

At block 130, selected multi-dimensional signals are monitored during unknown conditions for detecting a patient condition. At block 132, one or more stored templates are used for computing compensated signals from one or more of the multi-dimensional monitoring signals. As described above, multiple sensor signal grouping can result in multiple multi-dimensional signals. For each multi-dimensional signal, multiple compensated signals may be computed and used to extract multiple compensated feature sets. The compensated signal has fewer dimensions than a sensed multi-dimensional signal. In some cases, the compensated signal will contain less variation due to artifact and retains significant variation due to a variable of interest. The computed signal is thus "compensated" for artifact. In other cases, the compensated signal is computed to identify the most significant variation of the multi-dimensional signal corresponding to what is treated as an artifact condition by other PCA blocks. Operations performed at block 132 for computing a compensated signal may involve the use of previously stored templates for determining a correlation or template matching metric between a stored template and a multi-dimensional signal. Operations performed at block 132 for computing a compensated signal may include using a stored template to cancel artifact from a multi-dimensional signal.

At block 134, a processing module extracts signal features from the compensated signals and optionally from the uncompensated signals. At block 136, the medical device controller performs a patient condition detection algorithm using the compensated and uncompensated signal features. Numerous detection algorithms may be applied at block 136 which may involve threshold comparisons, statistical analysis, neural networks or other methods for detecting a patient condition from the compensated signal. In response to a detected condition, the controller may make therapy delivery decisions, store patient data, or initiate telemetric communication with another device.

FIG. 7 is a functional block diagram of a PCA processing module 66 according to one embodiment. PCA module 66 receives a multi-dimensional signal from signal conditioning module 60 as described above. Signal conditioning is performed by signal conditioning module 60 on the sensor signal set 54 to provide a digital, time-varying n-dimensional signal to training module 76. The signal conditioning operations will vary depending on the sensor signal set 54 received and the particular monitoring application.

Training module 76 determines and stores templates of principal components of variation of the n-dimensional signal under known conditions. Training is performed during selected intervals of time as indicated by training flag 72. Training intervals can be determined automatically using signals from sensor signal set 54 or manually identified by a patient or clinician when variable conditions are known, for example periods of a known cardiac rhythm, a known patient activity or activity level, a known patient posture, etc. During training, a principal component of the multi-dimensional signal is computed and updated using an incoming stream of signal data from signal conditioning module 60.

A convergence metric 74 may be computed using data provided by the training module 76. The convergence metric 74 may be updated as the principal component is updated in response to incoming streaming data. The convergence metric is used by the medical device controller to determine when the principal component computed by training module 250 has reached a "steady-state" for the known conditions. The convergence metric is used to determine when the variation in direction of the incoming n-dimensional data is occurring within an acceptable range so that the currently computed principal component is a reliable representation of that variation. The principal component is stored as a template of the signal response to the known condition (s) when the convergence metric indicates the signal data has converged within an acceptable range of variation.

As indicated above, the template may include one or more principal components which may include the first principal component of the signal data and/or one or more principal components orthogonal to the first principal component. Additional details regarding the operations performed by training module 76 will be described below in conjunction with FIG. 8.

A compensated signal module 78 receives an uncompensated signal from signal conditioning module 60. The uncompensated signal is received by compensated signal module 78 during unknown conditions for monitoring the patient and detecting a patient condition. In some embodiments, compensated signal module 78 also receives the uncompensated signal during known conditions when the training module 76 is determining and storing principal components. For example, as will be described below, the compensated signal module 78 provides data for determining convergence metrics for terminating a training interval. In other embodiments, signal processing module 66 operates in a training mode during training intervals of time identified by training flag 72 and operates in a monitoring mode during other intervals of time when training flag 72 is not present. When a training flag 72 is present indicating known conditions, training module 76 is enabled to perform PCA to generate and store a template of the signal.

When a training flag 72 is not present, PCA module 66 may be enabled by the medical device controller to monitor the multi-dimensional signal for detecting a patient condition. During monitoring, one or more stored principal component templates provided by training module 76 are used by compensated signal module 78 to convert the uncompensated signal received from signal conditioning module 60 to a compensated signal.

As indicated previously, the incoming uncompensated signal from signal conditioning module 60 may be thought of as an "uncompensated" signal in that it represents the signal data before adjustment of the data has been performed using the results of PCA. A compensated signal is computed by module 78 to adjust the monitoring signal using one or more principal component templates to extract a signal having fewer dimensions than the original multi-dimensional signal.

A compensated signal may represent a match or goodness of fit between the monitored incoming signal and a principal component of a variable of interest during known conditions. In this way, the compensated signal computed by module 78 can be thought of as a signal reflecting how well the monitoring signal matches a known condition. The compensated signal computed by module 78 may alternatively or additionally represent the incoming signal with artifact cancellation. In this case, the compensated signal represents the variation of the monitoring signal primarily due to a variable of interest with the influence of one or more artifacts removed or suppressed. Additional details regarding the operations of compensated signal module 78 will be described below in conjunction with FIG. 10. The compensated signal output from module 78 is provided to an uncompensated feature extraction block 68 as generally described above in conjunction with FIG. 5.

FIG. 8 is a functional block diagram of a training module 76 included in the PCA module 66 for computing principal component templates from a multi-dimensional signal. In PCA, a principal component of an n-dimensional signal response to known conditions is computed from a covariance matrix of the individual signal dimensions.

Prior to computing the covariance matrix, a mean signal value for each signal dimension is subtracted from the signal samples in each dimension to obtain a mean-removed signal. By subtracting the mean signal values in each signal dimension, the data will have a mean of zero which will center a principal component coordinate system at the origin as shown by the example in FIG. 2. This operation of removing the means from the multi-dimensional signal may be performed by the signal conditioning module 60. The mean-removed training signal (output of signal conditioning module 60) is used to compute a covariance matrix. Using a two-dimensional signal as an example, a training signal M having x- and y-dimensions is provided as a mean-removed signal, e.g., a bandpass filtered output of signal conditioning module 60, which can be expressed as a 1×2 matrix:

$$M = \begin{bmatrix} X - \bar{X} \\ Y - \bar{Y} \end{bmatrix} = \begin{bmatrix} X \\ Y \end{bmatrix}_{MR}$$

The mean-removed training signal may be acquired through digital filtering as described above. Alternatively, the mean-removed signal may be computed mathematically by subtracting a mean value from the individual digitized signal samples for a respective signal dimension. A mean value may be a running mean computed from a desired number of signal samples or signal samples acquired over a desired interval of time.

In FIG. 8, the training signal 226 is provided as input to covariance matrix module 252. The training signal 226 is the uncompensated multi-dimensional signal received from the signal conditioning block 60 during a training interval identified by an enabled training flag. In covariance matrix module 252, an outer product block 254 computes the covariance matrix of the training signal. Since the signal means have already been subtracted from the data, the covariance matrix can be computed as the outer product of the training signal matrix M and its transpose:

$$\mathrm{cov}[M] = \mathrm{mean}([M][M]^T)$$

Computation of the covariance matrix can be shown mathematically as:

$$\mathrm{mean}\left(\begin{bmatrix} X \\ Y \end{bmatrix} \otimes [X\ Y]\right) = \mathrm{mean}\left(\begin{bmatrix} (X*X) & (X*Y) \\ (Y*X) & (Y*Y) \end{bmatrix}\right)$$

The main diagonal of the covariance matrix corresponds to the variances of the individual signal dimensions. The upper left value corresponds to the variance in the x-dimension and the lower right value corresponds to the variance of the y-dimension. The covariance matrix is symmetrical about the main diagonal since cov(Y,X) is equal to cov(X,Y). While a 2×2 covariance matrix computed from a 1×2 signal is shown, it is to be understood that the training signal may be any 1×n signal matrix corresponding to an n-dimensional sensor set signal. The resulting covariance matrix is an n×n covariance matrix.

In one embodiment, the covariance matrix is filtered at block 256, which may be a first order low pass filter. Each individual element of the covariance matrix is filtered using a filter time constant, tau, 258. The filter time constant 258 is selected according to an expected frequency of the variable of interest or the artifact for which the template is being generated, thus providing a cleaner signal from which the template will be computed. For example, if the principal component for a cardiac variable is desired during normal sinus rhythm, the time constant 258 may be set long enough to allow the covariance matrix to be filtered with a frequency that retains signal variations that occur with the cardiac variable, e.g. at a frequency centered around approximately 1 Hz, and filters variations that occur at other frequencies due to artifacts such as respiration or body motion. If the principal component for respiration artifact is desired for use in artifact cancellation, the time constant 258 may be set to retain signal variations that occur at the expected frequency of the patient's respiration and filter other frequency variation such as cardiac pulsatility variations. If the principal component for body motion variation is desired, the time constant 258 may be set to retain the frequency of the body motion signal, e.g. derived from an activity sensor, and filter other signal variation frequencies.

The selection of the time constant 258 can be thought of as setting a window of time over which a filtered covariance matrix is generated from a stream of computed covariance matrices. As such, time constant 258 is inversely related to the frequency of the variable for which the principal component is being computed.

The time constant 258 may be selected based on input from other sensors 255. For example, a respiration signal, an activity signal, or other sensor signal input may be received by the medical device controller to select the appropriate time constant 258 to be inversely proportional to the frequency of the variable condition for which the principal component is being computed. In one embodiment, when filtering a respiration artifact signal, the time constant 258 may be set using input from an activity sensor such that the time constant 258 is set to a shorter time interval when activity is high and the respiration rate is expected to be high. Similarly, time constant 258 is set to a relatively longer time interval when activity is low and the respiration rate is expected to be low.

Using the filtered covariance matrix, template module 270 computes the principal components of the covariance matrix. Template module 270 is enabled in response to training condition flag 72 which indicates a state of known condition(s) is detected. Flag 72 may be generated automatically by the medical device controller in response to input from other sensors 255, any of the sensor set 54 used to obtain training signal 226, or in response to a user-entered command.

Template module 270 includes a singular value decomposition (SVD) block 272. SVD block 272 performs a factorization operation on the covariance matrix received from covariance matrix module 252 to determine the eigenvector matrix and the eigenvalue matrix for the covariance matrix. For an n×n covariance matrix, an n×n eigenvector matrix is derived which includes n eigenvectors in the columns of the matrix. The n eigenvectors are orthogonal unit vectors extending from the origin of the n-dimensional coordinate system and represent patterns of the multi-dimensional data. In particular, one column of the eigenvector matrix corresponding to the greatest eigenvalue will be a vector defining an axis along which the greatest variation of the signal data occurs for the current variable conditions, i.e., the first principal component.

The eigenvalue matrix is an n×n diagonal matrix containing the squares of the eigenvalues for the eigenvectors along its diagonal. The eigenvalue matrix column containing the greatest eigenvalue indicates the most significant relationship between the signal dimensions. The largest eigenvalue can thus be used to identify the eigenvector defining the first principal component of the signal data for the known conditions. When n-dimensional signal data is acquired, the eigenvectors corresponding to the greatest eigenvalues may be selected and other eigenvectors, associated with the least significant variation of the signal data, may be ignored, allowing the number of dimensions to be reduced in an analysis of the data.

At block 274, the greatest eigenvalue is extracted. At block 276, the column of the eigenvector matrix corresponding to the column in which the greatest eigenvalue is present is extracted as the first principal component of the signal data. Other signal components defined by the other eigenvectors may be ignored. In alternative embodiments, two or more eigenvectors may be extracted at block 276 based on identifying the greatest eigenvalues.

The greatest eigenvalue may be required to be greater than other eigenvalues by a predetermined amount in order to extract a first principal component. For example, the greatest eigenvalue may be required to be at least 10 times greater than other eigenvalues in order to accept the corresponding eigenvector as the first principal component and ignore all other principal components. If no eigenvalues reach criteria for selecting a first principal component, no template is stored for the current variable conditions.

The output of template module 254 is the derived first principal component of the signal data and is stored as a template 260 for the known conditions. In other words, the principal component template 260 defines an axis extending through the n-dimensional coordinate system along which the greatest variation of the multi-dimensional signal occurs in response to the known conditions.

While extraction block 276 indicates only the first principal component is extracted, it is to be understood that other principal components may be extracted in addition to or alternatively to the first principal component. Thus the template 260 may represent multiple principal components for known conditions or a single principal component, which may be the first principal component or a principal component orthogonal to the first principal component.

In one embodiment, convergence metrics 74 are computed during the training mode to determine when a principal component template 260 can be stored based on the convergence of the training signal data. One or more convergence metrics 74 may be provided by covariance matrix module 252 and/or template module 270. In one embodiment, the variances of the individual signal dimensions (along the main diagonal of the covariance matrix) may be provided by outer product block 254 to be used as convergence metrics. For example the variance of x- and y-dimensions of a two dimensional signal and/or covariances of these signal dimensions may be compared to an acceptable range. Once the convergence metric(s) remain within an acceptable range, the principal component(s) extracted at block 276 is stored as the template 260 for the currently known conditions.

In another embodiment, the greatest eigenvalue extracted at block 274 may be provided to the medical device controller for use as a convergence metric. One or more convergence metrics may be computed or derived from any of the eigenvalues or eigenvectors computed by SVD block 272. The medical device controller determines when the convergence metric(s) 74 have reached a steady state, i.e., vary within an acceptable range. Upon detecting convergence, the template 260 is stored for the known conditions.

Training module 76 may be implemented to respond to training flag 72 for acquiring a template corresponding to a variety of known conditions. Variable conditions may relate to multiple states for a given variable or different combinations of variables. For example, a template may be stored for normal sinus rhythm at rest, normal sinus rhythm at different activity levels (e.g., low, moderate and high levels of exertion) or different types of activity (e.g., walking, climbing stairs, etc.), different body postures, and during known arrhythmias such as VT, VF or atrial tachycardias. As long as training condition flag 72 is active or high, the training module operates to derive the principal components of the training signal until convergence criteria are satisfied and the template is stored. If the training condition flag 72 is inactive or low before the controller determines that convergence has been reached based on the convergence metrics 74, template module 270 may terminate computation of the principal components of the signal data without storing a template. A training flag 72 may be removed before template storage is complete due to detection of a change in the known conditions based on sensor input or a user-entered command.

In some embodiments, updating of principal component templates may be performed in response to detecting a change in patient conditions. For example, a training flag may be set in response to determining that the patient is at rest. The training module 76 responds by computing a principal component from streaming data corresponding to the resting condition of the patient. When the patient activity changes, the training flag may be removed to allow the computed principal component to be stored for the resting condition. The training flag may then be reset to allow the principal component to be updated for the new level of patient activity until a change in activity is detected again. As such, a training flag may be set, removed and reset in response to a physiological signal to control the times at which computation of a principal component from streaming data is initiated and when computed principal component values are locked in and stored as a template. In another embodiment, principal component computation may operate continuously with the training flag, and optionally convergence metrics, indicating when component values should be stored based on detected variable conditions.

Figure 9:
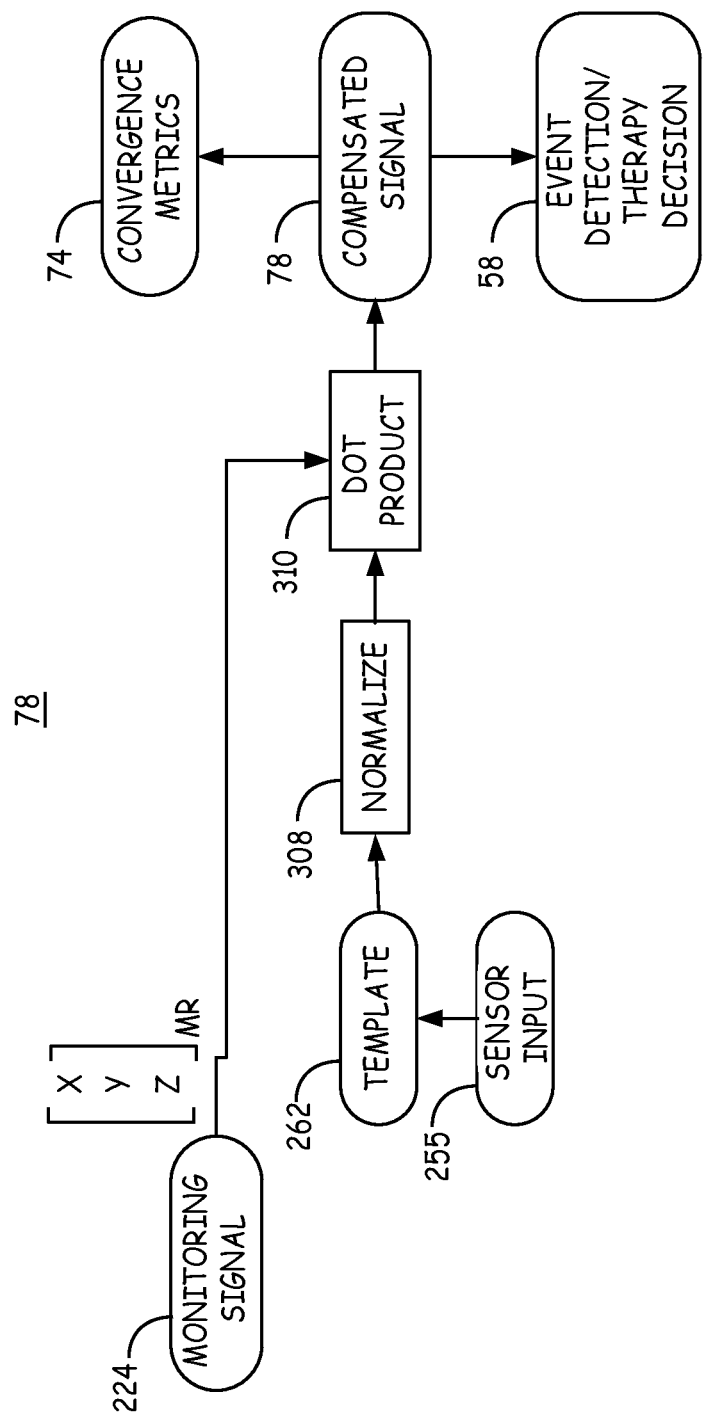
FIG. 9 is a functional block diagram of one embodiment of a compensated signal module of FIG. 7.

FIG. 9 is a functional block diagram of one embodiment of a compensated signal module 78 of FIG. 7. During a monitoring mode of operation, the signal processing module 56 of FIG. 5 monitors the mean-removed signal output of signal conditioning module 60 (FIG. 7) to detect a patient condition. The output of signal processing conditioning module 60 is provided as a mean-removed (MR) monitoring signal 224 to compensated signal module 78. As mentioned previously, a compensated signal is a signal computed using the monitoring signal 224 (the uncompensated signal) and a stored template 262.

A template 262 used for computing the compensated signal may be selected based on the patient condition being monitored. For example, if the n-dimensional sensor signal is to be used for verifying VF detection, the template 262 may be selected as the template corresponding to the first principal component of the signal data during normal sinus rhythm conditions. The compensated signal may provide a comparison of the monitoring signal 224 and the template 262.

Alternatively, template 262 may be selected according to artifact desired to be cancelled. For example, template 262 may correspond to a principal component determined for a known artifact condition. The principal component may be a first principal component or one of the principal components orthogonal to the first principal component. When a principal component orthogonal to the first principal component of the signal data during a known artifact condition is used to compute a compensated signal, the artifact condition is cancelled or suppressed from the compensated signal. By using a template of a principal component orthogonal to the first principal component in subsequent matrix calculations, the contribution of artifact can effectively be subtracted from the multidimensional signal.

The template 262 provided to compensated signal module 78 may be selected based on other sensor input 255. For example, sensor input 255 may include patient activity, posture, respiration, ECG or other information that allows an appropriate template 262 to be selected for the current variable conditions. In the case of monitoring a patient cardiac rhythm for verifying a VT detected using ECG signals, the medical device controller may check the patient activity and/or posture to select a template that was acquired during similar patient activity or posture. For example, if the activity signal indicates the patient is climbing stairs, template 262 is selected as the template stored during similar activity conditions to allow the body motion artifact to be cancelled or suppressed in the compensated signal.

At block 308, the template is normalized to be a unit vector. In some embodiments, this normalization block 308 is not required if the template has already been normalized by training module 76. The results of singular value decomposition software algorithms are typically provided as normalized eigenvectors, making normalization block 308 unnecessary in some embodiments.

The normalized template and the monitoring signal are provided as input to block 310. Generally, block 310 computes a compensated signal 312 using the normalized template and the monitoring signal. The compensated signal 312 is used by the medical device controller for detecting a patient event or condition at block 314.

In one embodiment, block 310 computes a dot product of the normalized template and the monitoring signal 224. The dot product is a scalar output and thus block 310 reduces the n-dimensional signal to a one-dimensional signal. For example, the dot product operation performed at block 310 may be the dot product of a normalized template representing the first principal component for a known condition and the monitoring signal. The resulting one-dimensional signal will represent the match between the template and the monitoring signal. The dot product will be zero when the two vectors (i.e., the template and the monitoring signal at a sample time point) are orthogonal and will approach the amplitude of the monitoring signal when the two vectors are in close alignment.

Alternatively, the dot product operation performed at block 310 may be the dot product of the monitoring signal and a principal component template orthogonal to one or more principal component for an artifact condition. Since the dot product of two orthogonal vectors is zero, artifact can be removed from the monitoring signal in the resulting compensated signal 312. The dot product will represent the effect of removing the first principal component of the artifact from the incoming monitoring signal. This approach may be used for canceling artifact in the monitoring signal. For example, if cancellation of body motion artifact is desired, the dot product computed at block 310 may be computed using the monitoring signal and a principal component template orthogonal to the first principal component determined for a known condition for body motion. The compensated signal 312 will then represent the monitoring signal with the body motion artifact removed, allowing analysis of the compensated signal for detecting a patient condition associated with the variable of interest with the influence of artifact effectively subtracted.

In some embodiments, the compensated signal is computed from the streaming data simultaneously during computation of a template by the training module 76 of FIG. 7 and provided for computing a convergence metric 74. A convergence metric 74 may be a comparison of the variance of the compensated signal to the variance of individual dimensions received by the training module 76. When the variance of the convergence metric is within predetermined limits as compared to the variances of the individual dimensions, the controller may cause the training module 76 to store the currently computed template for the existing variable conditions. The training module 76 stops computing the template, and compensated signal module 78 continues to compute compensated signal 78 using the stored template.

The compensated signal 78 is used to extract compensated signal features which may include goodness-of-fit (or lack-of-fit) metrics at block 58 in an event detection algorithm. Numerous detection algorithms may be developed for analyzing the compensated signal 78 and for extracting features used for detecting a patient's physiological condition. Such algorithms may determine a match of the compensated signal with a normal patient condition or with a disease state. Detection algorithms may utilize morphological comparisons between the compensated signal and known signal characteristics for a known patient condition, statistical methods, neural networks, or other models for determining a patient condition represented by the compensated signal. Generally, a detection algorithm may derive metrics from the compensated signal that are compared to a detection threshold or range.

Figure 10:
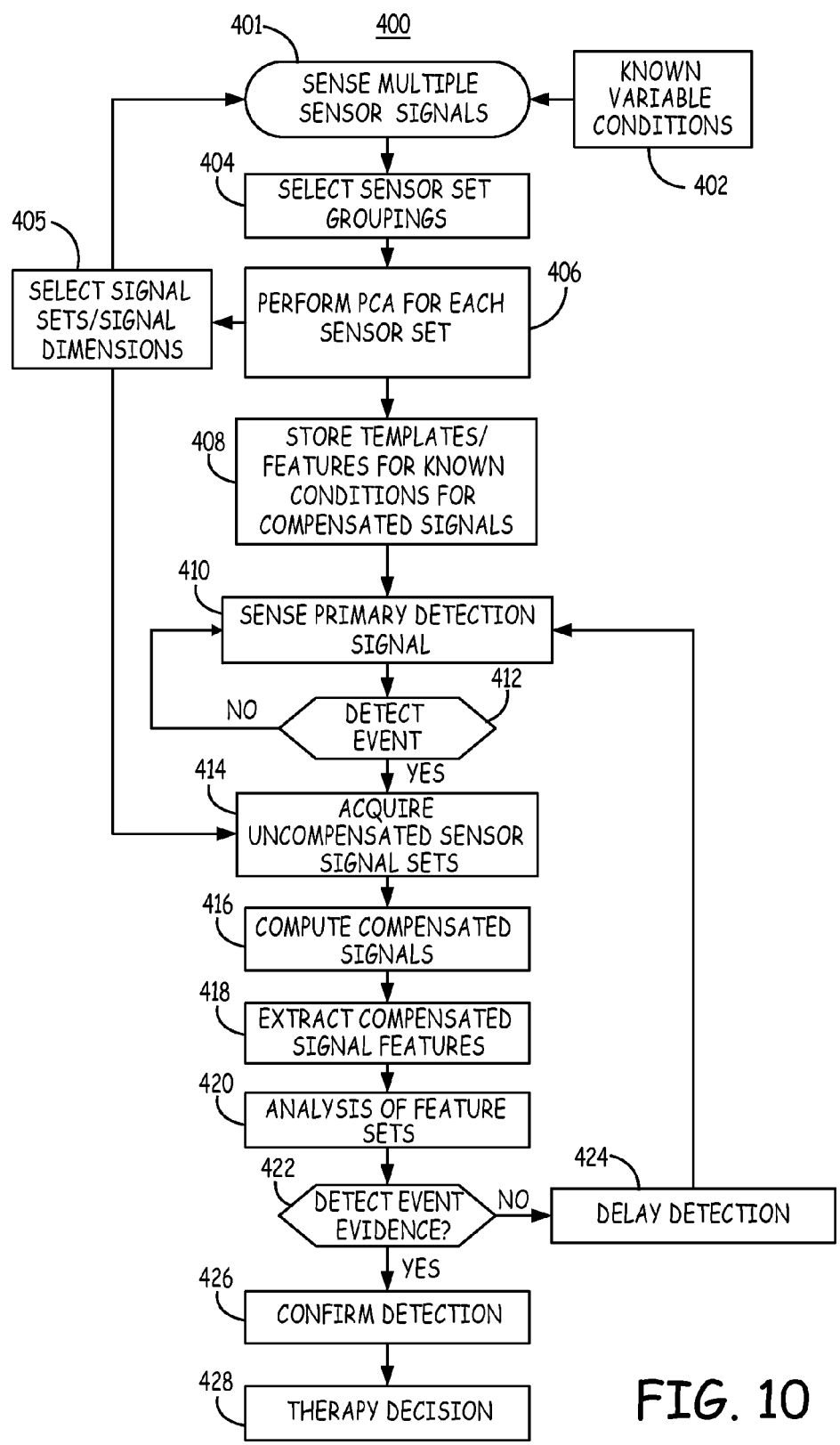
FIG. 10 is a flow chart of one method for signal processing and analysis using multiple multi-dimensional signals and PCA for detecting a patient condition.

FIG. 10 is a flow chart 400 of one method for signal processing and analysis using multiple multi-dimensional signals and PCA for detecting a patient condition. At block 401, multiple sensor signals are sensed during known conditions 402. The sensor signals are grouped into sensor sets at block 404 to form a number of multi-dimensional signals. A signal from a single sensor may be used in more than one grouping to form the multiple multi-dimensional signals. PCA is performed at block 406 as described above to compute a template for the known conditions. It is recognized that, for a given set of variable conditions, a template may include storing more than one principal component. The stored template may include the first principal component and/or one or more other principal components orthogonal to the first principal component.

Signal dimensions to be sensed or used during signal processing may be selected at block 405 based on the results of the PCA at block 406. The medical device controller may disable a sensor producing extraneous signals or cause the signal processing circuitry to ignore a signal dimension if that signal dimension is not contributing to the variation of an n-dimensional signal along a principal component. The value computed for that dimension in the principal component vector will be zero. In other words, the principal component will be defined by an eigenvector having a zero (or near zero value) in at least one dimension, e.g., [x, y, 0]. The sensor or signal corresponding to a signal dimension having a zero contribution to a principal component, i.e. an extraneous signal, can be disabled at block 405 or ignored during signal processing. Blocks 406 and 408 are performed for each of the sensor sets. The results of the PCA may be used to select which sensor sets are used for monitoring for a patient condition.

Blocks 401 through 408 may be repeated for a number of known conditions which may include known conditions for a variable of interest and/or known conditions for one or more artifacts. The results of PCA for the various known conditions may also be used in selecting which sensor sets are used at various times for detecting a patient condition. For example, one sensor signal group may demonstrate greater discrimination between normal sinus rhythm and an arrhythmia during a particular known condition, e.g. a particular patient activity, than another sensor signal group. In another example, one sensor set may demonstrate greater discrimination between a heart failure condition and a normal condition during a particular patient posture.

After storing templates and features for the multiple sensor signal sets at block 408, monitoring for patient conditions or events begins at block 410. Blocks 401 through 408 correspond generally to the training mode of operation described above, which may occur at scheduled times or in response to detecting known conditions using uncompensated sensor signals. Once an initial set of templates and/or features are stored at block 408, blocks 401 through 408 may be repeated at any time during or intermittently with event monitoring.

At block 410, a primary detection signal is monitored for making an initial detection of a patient condition. The primary detection signal may be an uncompensated signal. For example, R-R intervals measured from the sensed ECG signal may be analyzed and compared to arrhythmia detection criteria. The primary detection signal may be a single or multiple uncompensated signals that are monitored in a continuous or periodic manner for making an initial event detection. In some embodiments, the primary detection signal may be a multi-dimensional signal analyzed using PCA. Results of PCA of the primary signal may be compared to a stored template or signal feature corresponding to the patient event being detected.

If an event is detected based on the primary detection signal at block 412, the IMD controller enables monitoring of selected multi-dimensional signals at block 414. The multi-dimensional signals acquired at block 414 may be selected based on other patient conditions that may be known based on uncompensated signals. For example, patient activity, patient posture, heart rate or other known conditions at the time of the preliminary event detection at block 412 may determine which sensor signal sets are selected (block 405) for acquiring uncompensated signals at block 414.

Multi-dimensional signals obtained according to selected sensor signal sets and corresponding stored templates can be used to compute compensated signals at block 416. The compensated signals may be artifact-compensated signals generally computed by determining a dot product of a multi-dimensional signal and an artifact template stored at block 408 to produce a 1-dimensional (or other reduced dimensionality) signal with artifact variation removed. It is recognized that in varying embodiments, multiple compensated signals may be computed from a sensor signal set as described above using the uncompensated signal and one or more stored templates. Furthermore, multiple compensated signals from each of the sensor signal sets may be determined.

The compensated signals are analyzed at block 418 to extract compensated signal features. As described above, multiple features sets may be extracted from each sensor signal set. At block 420 the extracted features are analyzed for evidence of the patient event. Features may include those extracted from uncompensated signal sets as well as the compensated signals. The analysis performed at block 420 will depend on the features extracted and may include threshold comparisons or other analysis of the extracted features.

If evidence supporting the preliminary event detection is detected at block 422, the event is confirmed at block 426 and the IMD controller can make an appropriate decision to deliver or adjust a therapy at block 428. If evidence supporting the event detection is not detected in the compensated signal features, the IMD controller may delay or cancel the event detection at block 424. The process may return to block 410 to perform further sensing and analysis of the primary detection signal and optionally other sensor signals to either reconfirm the event detection or confirm the preliminary detection was false.

Blocks 410 through 422 may be repeated when the results from the primary detection signal and the compensated signal analysis are confounding. A different set of sensor signals may be selected to in response to confounding results to confirm or invalidate a preliminary event detection.

The analysis of the multiple signal feature sets may include using weighted sums of extracted feature values or Boolean logic decisions and rules applied to the extracted features for determining if the event is detected. Rules for detecting the event may be refined over time in a learning process. Event detection rules may be applied in an adaptive process in which rules are selected in accordance with time-varying selection of sensor signal set groupings based on analysis of uncompensated and compensated signal features. For example, the selected sensor signal sets may vary depending on analysis of compensated and uncompensated signals and as the sensor signal set selection changes, event detection rules are selected accordingly.

Thus, signal processing methods and apparatus for use in a medical device for monitoring a patient have been presented in the foregoing description with reference to specific embodiments. It is appreciated that various modifications to the referenced embodiments may be made without departing from the scope of the disclosure as set forth in the following claims.

The invention claimed is:

1. A medical device, comprising:
a sensor module for sensing a plurality of physiological signals
a signal grouping module receiving the plurality of physiological signals and grouping the plurality of physiological signals into a plurality of multi-dimensional signals;
a plurality of processing modules each receiving one of the plurality of multi-dimensional signals, each of the plurality of processing modules configured to extract a first feature set from the plurality of multi-dimensional signals, perform principal component analysis of the plurality of multi-dimensional signals to compute principal components of variation for each of the plurality of multi-dimensional signals, and extract a second feature set from the principal components; and
a controller receiving the first feature set and the second feature set from at least one of the plurality of processing modules, the controller responsive to the first feature set and the second feature set to detect a physiological event, wherein the controller detects the event using a weighted combination of the first set and the second set of extracted features.

2. The device of claim 1 wherein the plurality of processing modules are further configured to compute a compensated signal from the principal components computed for a respective one of the plurality of multi-dimensional signals, the compensated signal having a reduced dimensionality as compared to the respective multi-dimensional signal, and extract the second feature set from the compensated signal.

3. The device of claim 1 wherein the signal grouping module is configured to group the plurality of physiological signals in response to a signal from the controller corresponding to a detected event.

4. The device of claim 1 wherein the controller detects the event using a Boolean logic rule applied to the first set and the second set of extracted features.

5. The device of claim 1 wherein the plurality of processing modules are further configured to identify an extraneous signal in one of the plurality of multi-dimensional signals in response to the computed principal components, and wherein the sensor module is configured to disable sensing of a physiological signal in response to one of the plurality of processing modules identifying the extraneous signal.

6. A medical device, comprising:
a sensor module for sensing a plurality of physiological signals
a signal grouping module receiving the plurality of physiological signals and grouping the plurality of physiological signals into a plurality of multi-dimensional signals;
a plurality of processing modules each receiving one of the plurality of multi-dimensional signals, each of the plurality of processing modules configured to extract a first feature set from the plurality of multi-dimensional signals, perform principal component analysis of the plurality of multi-dimensional signals to compute principal components of variation for each of the plurality of multi-dimensional signals, and extract a second feature set from the principal components; and
a controller receiving the first feature set and the second feature set from at least one of the plurality of processing modules, the controller responsive to the first feature set and the second feature set to detect a physiological event, wherein the signal grouping module is configured to group the plurality of physiological signals in response to one of the first feature set and the second feature set.

7. A medical device, comprising:
a sensor module for sensing a plurality of physiological signals
a signal grouping module receiving the plurality of physiological signals and grouping the plurality of physiological signals into a plurality of multi-dimensional signals;
a plurality of processing modules each receiving one of the plurality of multi-dimensional signals, each of the plurality of processing modules configured to extract a first feature set from the plurality of multi-dimensional signals, perform principal component analysis of the plurality of multi-dimensional signals to compute principal components of variation for each of the plurality of multi-dimensional signals, and extract a second feature set from the principal components; and
a controller receiving the first feature set and the second feature set from at least one of the plurality of processing modules, the controller responsive to the first feature set and the second feature set to detect a physiological event, wherein the sensor module comprises a plurality of physiological sensors and is configured to selectively enable a physiological sensor in response to the extracted first feature set and the second feature set.

8. The device of claim 7 wherein the controller is further configured to detect a known patient condition in response to one of a physiological sensor signal and patient input, and enable a training flag in response to the known patient condition, wherein one of the plurality of processing modules is configured to receive the training flag and compute a template of one of the multi-dimensional signals corresponding to the known patient condition, the controller being configured to use the template in computing the compensated signal.

9. A method, comprising:
sensing a plurality of physiological signals
grouping the plurality of physiological signals into a plurality of multi-dimensional signals;
extracting a first feature set from the plurality of multi-dimensional signals;
performing principal component analysis of each of the plurality of multi-dimensional signals to compute principal components of variation for each of the plurality of multi-dimensional signals;
extracting a second feature set from the computed principal components; and
detecting a physiological event in response to the first feature set and the second feature set, wherein detecting the event comprises using a weighted combination of the first set and the second set of extracted features.

10. The method of claim 9 further comprising:
computing a compensated signal from the principal components compute for one of the plurality of multi-dimensional signals, the compensated signal having a reduced dimensionality as compared to the respective multi-dimensional signal, and extracting the second feature set from the compensated signal.

11. The method of claim 9 further comprising grouping the plurality of physiological signals in response to a detected event.

12. The method of claim 9 further comprising selectively enable a physiological sensor in response to the signal grouping.

13. The method of claim 10 further comprising
detecting a known patient condition in response to one of a physiological sensor signal and patient input; and
enabling a training flag in response to the known patient condition;
computing a template of one of the multi-dimensional signals corresponding to the known patient condition using principal component analysis, and
using the template to compute the compensated signal.

14. The method of claim 9 further comprising detecting the event using a Boolean logic rule applied to the first set and the second set of extracted features.

15. The method of claim 9 further comprising:
identifying an extraneous signal in one of the plurality of multidimensional signals in response to the computed principal components, and
disabling sensing of one of the plurality of physiological signals in response to identifying the extraneous signal.

16. A method, comprising:
sensing a plurality of physiological signals
grouping the plurality of physiological signals into a plurality of multi-dimensional signals;
extracting a first feature set from the plurality of multi-dimensional signals;
performing principal component analysis of each of the plurality of multi-dimensional signals to compute principal components of variation for each of the plurality of multi-dimensional signals;
extracting a second feature set from the computed principal components; and
detecting a physiological event in response to the first feature set and the second feature set, further comprising grouping the plurality of physiological signals in response to one of the first feature set and the second feature set.

17. A non-transitory computer readable medium storing a set of instructions which when implemented in a medical device system cause the system to:
sense a plurality of physiological signals;
group the plurality of physiological signals into a plurality of multi-dimensional signals;
extract a first feature set from the plurality of physiological signals;
perform principal component analysis of each of the plurality of multi-dimensional signals to compute principal components of variation for each of the plurality of multi-dimensional signals;
extract a second feature set from the computed principal components; and
detect a physiological event in response to the first feature set and the second feature set, wherein the detecting the event comprises using a weighted combination of the first set and the second set of extracted features.

* * * * *